United States Patent
Candau

(10) Patent No.: US 7,357,920 B2
(45) Date of Patent: *Apr. 15, 2008

(54) PHOTOSTABLE PHOTOPROTECTIVE COMPOSITIONS COMPRISING DIBENZOYLMETHANE AND AMIDE OIL COMPOUNDS AND A COMPOUND THAT ACCEPTS THE EXCITED TRIPLET LEVEL ENERGY OF SAID DIBENZOYLMETHANE(S)

(75) Inventor: Didier Candau, Bievres (FR)

(73) Assignee: L'Oreal, Paris (FR)

( * ) Notice: Subject to any disclaimer, the term of this patent is extended or adjusted under 35 U.S.C. 154(b) by 238 days.

This patent is subject to a terminal disclaimer.

(21) Appl. No.: 11/249,398

(22) Filed: Oct. 14, 2005

(65) Prior Publication Data

US 2006/0083698 A1   Apr. 20, 2006

Related U.S. Application Data

(60) Provisional application No. 60/623,034, filed on Oct. 29, 2004.

(30) Foreign Application Priority Data

Oct. 19, 2004 (FR) .................................. 04 52367

(51) Int. Cl.
*A61Q 17/04* (2006.01)
*A61Q 17/00* (2006.01)
*A61Q 19/04* (2006.01)
*A61Q 19/00* (2006.01)
*A61K 8/02* (2006.01)

(52) U.S. Cl. .......................... 424/59; 424/60; 424/400; 424/401

(58) Field of Classification Search .................. 424/59, 424/60, 400, 401

See application file for complete search history.

(56) References Cited

U.S. PATENT DOCUMENTS 5,672,337 A   9/1997   Ascione et al.
5,882,633 A   3/1999   Pisson et al.
2004/0057916 A1   3/2004   Bonda et al.
2004/0170660 A1   9/2004   Wendel et al.
2005/0065251 A1   3/2005   Candau et al.

FOREIGN PATENT DOCUMENTS

| AU | B-60074/96 | 1/1997 |
|---|---|---|
| DE | 196 48 819 A1 | 5/1998 |
| EP | 0 717 982 A1 | 6/1996 |
| EP | 0928608 A2 | 7/1999 |
| JP | A 8-225436 | 9/1996 |
| JP | A 10-175837 | 6/1998 |
| JP | A 10-511982 | 11/1998 |
| JP | A 11-240828 | 9/1999 |
| JP | A 11-246841 | 9/1999 |
| JP | A 2002-540135 | 11/2002 |
| WO | WO 00/57850 | 10/2000 |
| WO | WO 03/007906 A1 | 1/2003 |
| WO | WO 03/039447 A2 | 5/2003 |
| WO | WO 03/103622 A1 | 12/2003 |
| WO | WO 2004/026197 A2 | 4/2004 |

OTHER PUBLICATIONS

French Search Report corresponding to FR 04/52367, issued on Jun. 13, 2005, 3 pages.
English Translation of Notice of Reasons for Rejection for corresponding Japanese Application No. 2005-303400.
English Translation of Search Report for corresponding FR 04/52367.

*Primary Examiner*—Shelley A. Dodson
(74) *Attorney, Agent, or Firm*—Buchanan, Ingersoll & Rooney, PC

(57) ABSTRACT

Topically applicable, improvedly photostabilized, photoprotective cosmetic/dermatological compositions contain (i) an effective UV-screening amount of at least one dibenzoylmethane sunscreen and an effective photostabilizing amount of (ii) at least one oil containing at least one amide structural unit and (iii) at least one compound accepting the excited triplet level energy of said at least one dibenzoylmethane sunscreen, formulated into (iv) a topically applicable, cosmetically/dermatologically acceptable support therefor.

52 Claims, No Drawings

PHOTOSTABLE PHOTOPROTECTIVE COMPOSITIONS COMPRISING DIBENZOYLMETHANE AND AMIDE OIL COMPOUNDS AND A COMPOUND THAT ACCEPTS THE EXCITED TRIPLET LEVEL ENERGY OF SAID DIBENZOYLMETHANE(S)

CROSS-REFERENCE TO PRIORITY/PCT/PROVISIONAL APPLICATIONS

This application claims priority under 35 U.S.C. § 119 (a)-(d) of FR 04/52367, filed Oct. 19, 2004, and claims benefit under 35 U.S.C. § 119(e) of provisional application No. 60/623,034, filed Oct. 29, 2004, each hereby expressly incorporated by reference and each assigned to the assignee hereof.

CROSS-REFERENCE TO COMPANION APPLICATIONS

Copending application Ser. Nos. 11/249,521 and 11/249,304, filed concurrently herewith and also assigned to the assignee hereof.

BACKGROUND OF THE INVENTION

1. Technical Field of the Invention

The present invention relates to photoprotective compositions for topical application containing a dibenzoylmethane derivative, an oil containing in its structure at least one amide unit more fully described hereinbelow and a compound capable of accepting the excited triplet level energy of the said dibenzoylmethane derivative.

The present invention also relates to a process for photostabilizing at least one dibenzoylmethane derivative against UV radiation via a combination of a an amide oil compound and a compound capable of accepting the excited triplet level energy of the said dibenzoylmethane derivative.

2. Description of Background and/or Related and/or Prior Art

It is known that light radiation with wavelengths of from 280 nm to 400 nm permits tanning of the human epidermis and that light rays with wavelengths more particularly from 280 to 320 nm, known as UV-B rays, cause skin burns and erythema which can harm the development of a natural tan. For these reasons, as well as for aesthetic reasons, there is a constant demand for means of controlling this natural tanning in order thus to control the color of the skin; this UV-B radiation should thus be screened out.

It is also known that UV-A rays, with wavelengths from 320 to 400 nm, which cause tanning of the skin, are liable to induce adverse changes therein, in particular in the case of sensitive skin or skin which is continually exposed to solar radiation. UV-A rays cause in particular a loss of elasticity of the skin and the appearance of wrinkles leading to premature aging of the skin. Same promote triggering of the erythemal reaction or amplify this reaction in certain individuals and may even be the cause of phototoxic or photoallergic reactions. Thus, for aesthetic and cosmetic reasons such as the conservation of the skin's natural elasticity, for example, an increasingly large number of individuals wish to control the effect of UV-A rays on their skin. It is thus desirable also to screen out UV-A radiation.

For the purpose of protecting the skin and keratin materials against UV radiation, anti-sun/sunscreen compositions comprising organic screening agents that are active in the UV-A range and in the UV-B range are generally employed. The majority of these screening agents are liposoluble.

In this respect, one particularly advantageous family of UV-A screening agents currently consists of dibenzoylmethane derivatives, and in particular 4-tert-butyl-4'-methoxydibenzoylmethane, which are liposoluble and have high intrinsic absorbing power. These dibenzoylmethane derivatives, which are compounds which are now well known per se as screening agents that are active in the UV-A range, are described in particular in FR-A-2,326,405 and FR-A-2,440,933, as well as in EP-A-0,114,607; 4-tert-butyl-4'-methoxy-dibenzoylmethane is moreover currently marketed under the trademark "Parsol 1789" by Roche Vitamins.

Unfortunately, it has been found that dibenzoylmethane derivatives are compounds that are relatively sensitive to ultraviolet radiation (especially UV-A), i.e., more specifically, they have an annoying tendency to be degraded more or less quickly under the action of this UV. Thus, this substantial lack of photochemical stability of dibenzoylmethane derivatives towards ultraviolet radiation, to which they are by nature intended to be subjected, does not make it possible to ensure constant protection during prolonged exposure to the sun, and so the user must make repeated applications at regular and close time intervals in order to obtain effective protection of the skin against UV rays.

To solve this technical problem, it has already been proposed in the prior art to combine dibenzoylmethane derivatives with compounds capable of accepting the excited triplet level energy of the said dibenzoylmethane derivative. This is the case, for example, for the naphthalene derivatives in U.S. Pat. Nos. 5,993,789, 6,113,931, 6,126,925 and 6,284,916. This is also the case for the fluorene derivatives as described in U.S. Published Application Nos. 2004/0057912, 2004/0057914, 2004/0057916 and 2004/06272. However, the photochemical stability of the dibenzoylmethane derivatives obtained with these compounds is still not fully satisfactory.

SUMMARY OF THE INVENTION

It has now been discovered, surprisingly, that by adding to the dibenzoylmethane derivatives mentioned above a combination of at least one amide oil of formula (I) more fully described hereinbelow and at least one compound capable of accepting the excited triplet level energy of the said dibenzoylmethane derivative, it is possible to substantially and remarkably improve the photochemical stability (or photostability) of these same dibenzoylmethane derivatives.

This essential discovery is the focus of the present invention.

Thus, the present invention features topically applicable cosmetic or dermatological compositions comprising, formulated into a cosmetically acceptable support:

(a) at least one dibenzoylmethane compound UV-screening agent, (b) at least one oil containing in its structure at least one amide unit of formula (I) more fully described hereinbelow;

(c) at least one compound capable of accepting the excited triplet level energy of the said dibenzoylmethane compound(s).

Throughout this text, the expression "oil containing in its structure at least one amide unit" will mean any compound comprising in its chemical structure at least one amide group (or function) of the type:

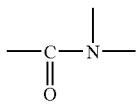

and simultaneously having the following characteristics:
a) liquid at 25° C.,
b) water-insoluble or water-immiscible at 25° C.,
c) has no emulsifying properties.

The present invention also features a process for improving the stability of at least one dibenzoylmethane derivative towards UV radiation, which entails adding to the said dibenzoylmethane derivative a combination of at least one oil containing in its structure at least one amide unit of formula (I) and at least one compound capable of accepting the excited triplet level energy of the said dibenzoylmethane derivative.

The invention also features the combination of at least one amide oil of formula (I) and of at least one compound capable of accepting the excited triplet level energy of a dibenzoylmethane compound in a cosmetic or dermatological composition comprising at least one dibenzoylmethane UV-screening agent, to improve the stability towards UV rays of the said dibenzoylmethane derivative.

Other characteristics, aspects and advantages of the invention will be seen from the detailed description that follows.

DETAILED DESCRIPTION OF BEST MODE AND SPECIFIC/PREFERRED EMBODIMENTS OF THE INVENTION

Among the dibenzoylmethane derivatives that are representative, in a non-limiting manner, are:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

Among the dibenzoylmethane derivatives mentioned above, 4-isopropyldibenzoylmethane will be used in particular, which is marketed under the name "Eusolex 8020" by Merck, and corresponds to the following formula:

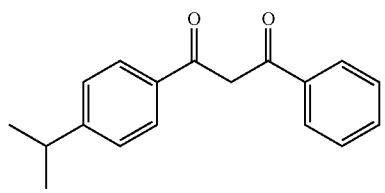

It is most particularly preferred to use 4-(tert-butyl)-4'-methoxydibenzoylmethane or Butyl Methoxy Dibenzoylmethane, marketed under the trademark "Parsol 1789" by Roche Vitamins; this screening agent corresponds to the following formula:

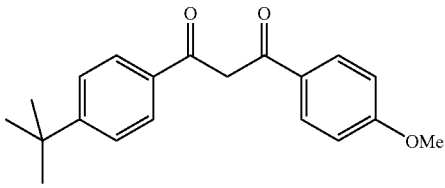

The dibenzoylmethane derivative(s) may be present in the compositions in accordance with the invention in contents preferably ranging from 0.01% to 10% by weight and more preferably from 0.1% to 6% by weight relative to the total weight of the composition.

The oil(s) containing in their structure at least one amide unit in accordance with the invention are selected from among the compounds of formula (I) below:

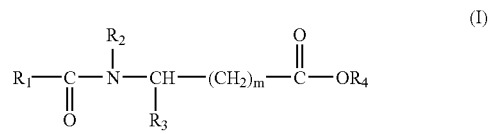

in which:
the radical $R_1$ is a saturated or unsaturated, aliphatic, cycloaliphatic or cyclic, optionally functionalized monovalent hydrocarbon-based radical having from 2 to 30 carbon atoms and preferably from 2 to 22 carbon atoms;
the radicals $R_2$, $R_3$ and $R_4$, which may be identical or different, are each hydrogen or saturated or unsaturated, aliphatic, cycloaliphatic or cyclic, optionally functionalized monovalent hydrocarbon-based radicals having from 1 to 30 carbon atoms and preferably from 1 to 22 carbon atoms;
m is 1 or 2.

As examples of saturated aliphatic hydrocarbon-based radicals, mention may be made especially of linear or branched, substituted or unsubstituted $C_1$-$C_{30}$ and preferably $C_1$-$C_{22}$ alkyl radicals, and in particular ethyl, n-propyl, isopropyl, n-butyl, isobutyl, tert-butyl, pentyl, n-amyl, isoamyl, neopentyl, n-hexyl, n-heptyl, n-octyl, 2-ethylhexyl, tert-octyl, decyl, lauryl and octadecyl radicals.

Examples of saturated cyclic hydrocarbon-based radicals that may especially be mentioned include cyclopentyl and cyclohexyl radicals, which are optionally substituted, in particular with alkyl radicals.

Examples of unsaturated aliphatic hydrocarbon-based radicals that may especially be mentioned include linear or branched, substituted or unsubstituted $C_2$-$C_{30}$ and preferably $C_2$-$C_{22}$ alkenyl or alkynyl radicals, and in particular vinyl, allyl, oleyl and linoleyl radicals.

Examples of unsaturated cyclic hydrocarbon-based radicals that may especially be mentioned include aryl radicals such as phenyl and naphthyl, which are optionally substituted, in particular with alkyl radicals, for instance the tolyl radical, and examples of unsaturated cycloaliphatic radicals that may be mentioned more particularly include benzyl and phenylethyl radicals.

The term "functionalized radicals" more particularly means radicals comprising in their chemical structure, either in the main chain or on a side chain unit, one or more functional groups especially of the ester, ether, alcohol, amine, amide or ketone type, but preferably esters.

The preferential amide oils of formula (I) are selected from among those in which:

$R_1$ is a linear or branched $C_2$-$C_{22}$ alkyl radical; a linear or branched $C_2$-$C_{22}$ alkenyl radical; an aryl radical;

$R_2$ is a hydrogen atom or a linear or branched $C_1$-$C_6$ alkyl radical;

$R_3$ is a hydrogen atom or a linear or branched $C_1$-$C_6$ alkyl radical;

$R_4$ is a linear or branched $C_1$-$C_{10}$ alkyl radical or a linear or branched $C_2$-$C_{10}$ alkenyl radical or a sterol residue.

In formula (I) presented above, the group $R_1(CO)$— is an acyl group of an acid preferably selected from the group consisting of toluic acid, capric acid, lauric acid, myristic acid, palmitic acid, stearic acid, behenic acid, linoleic acid, linolenic acid, oleic acid, isostearic acid, 2-ethylhexanoic acid, coconut oil fatty acids and palm kernel oil fatty acids. These acids may also contain a hydroxyl group.

In formula (I), the moiety —N($R_2$)CH($R_3$)($CH_2$)$_m$(CO)— of the amino acid ester is preferably selected from those corresponding to the following amino acids:

glycine, alanine, valine, leucine, isoleucine, serine, threonine, proline, hydroxyproline, β-alanine, N-butyl-β-alanine, aminobutyric acid, aminocaproic acid, sarcosine and N-methyl-β-alanine.

In formula (I), the moiety of the amino acid esters corresponding to the group $OR_4$ may be obtained from alcohols selected from the group consisting of methanol, ethanol, propanol, isopropanol, butanol, tert-butanol, isobutanol, 3-methyl-1-butanol, 2-methyl-1-butanol, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol and isostearyl alcohol.

The oils containing in their structure at least one amide function of formula (I) in accordance with the invention are known per se. Certain of which are especially described with their modes of preparation in EP-1,044,676 and EP-0,928,608 from the company Ajinomoto Co. Others are known in cosmetics as insect repellents, for instance N-acetyl N-butylaminopropionate or N,N-diethyltoluamide.

Among the compounds of formula (I) that are particularly preferred, use will be made of:

(1) Isopropyl N-lauroylsarcosinate of formula:

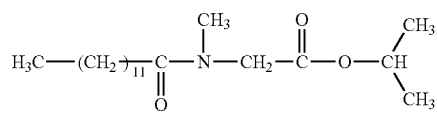

such as the product marketed under the Eldew SL-205 by Ajimoto.

The oil(s) containing in their structure at least one amide function as defined above are present in the compositions according to the invention in concentrations preferably ranging from 0.1% to 40% by weight and more preferentially from 1% to 20% by weight relative to the total weight of the composition.

According to the present invention, the amide oil(s) of formula (I) is(are) used in combination with a compound capable of accepting the excited triplet level energy of the said dibenzoylmethane derivative so as to deactivate the excited states of the dibenzoylmethane molecule excited under the influence of UV radiation and to allow it to regain its ground state.

According to one preferred embodiment, the compounds that accept the excited triplet level energy of the said dibenzoylmethane derivative have an excited triplet level energy ranging from 40 kcal/mol to 70 kcal/mol.

The excited triplet level energies may be determined via the techniques of oxygen perturbation or phosphorescence as described in the article by J. Gonzenbach, T. J. Hill and T. G. Truscott "The Triplet Energy Levels in UV-A and UV-B Sunscreens", *J. Photochem. Photobiol. B: Biol.*, Vol. 16, pages 337-379 (1992). The technique of oxygen perturbation consists in measuring the UV absorption spectrum of a compound when it is placed in an environment under a high pressure of oxygen: i.e., 2000 psi. Under these conditions, the spin selection rules are perturbed and the exposure of the compound to UV leads to the lowest excited triplet level by direct excitation of the ground state. The wavelength λ (in μm) at which the transition takes place is used to calculate the energy of the triplet level in kcal/mol via the formula E=28.635/λ, which is derived from the equation E=hv where E is the energy, h is Planck's constant and v is the frequency of the electromagnetic wave.

The technique of phosphorescence is based on the fact that many compounds emit phosphorescence during the deactivation of their excited triplet level. By measuring the wavelength at which the phosphorescence takes place, the excited triplet energy levels may be calculated as previously. The excited triplet energy levels may be determined by measuring the phosphorescence spectra of samples with a spectrophotometer equipped with a phosphorescence accessory. Such excited triplet levels have been widely reported, for example in the article by A. J. Gordon and R. A. Ford, "The Chemist Companion", *John Wiley & Sons*, pages 351-355 (1992).

The compounds of the excited triplet level of the said dibenzoylmethane derivative are selected, for example, from among:

(i) naphthalene derivatives such as those described in U.S. Pat. Nos. 5,993,789, 6,113,931, 6,126,925 and 6,284,916;

(ii) 4-hydroxybenzylidene malonate derivatives or 4-hydroxycinnamate derivatives such as those described in WO 03/007,906;

(iii) the fluorene derivatives as described in U.S. Published Application Nos. 2004/00579912, 2004/00579914, 2004/00579916 and 2004/062 726;

(iv) piperidinol salts such as those described in WO 03/007,906;

(v) mixtures thereof.

Among the naphthalene derivatives in accordance with the invention that will be used more preferentially are naphthalenedicarboxylic acid diesters and polyesters selected from among:

(i) the diesters of formula (II) below:

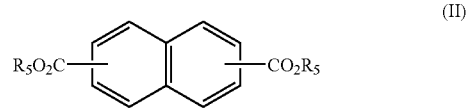

(ii) the diesters or polyesters of formula (III) below:

$$HO + R_7 - O_2C - \text{[naphthalene]} - CO_2 + R_6 - OH \quad \text{(III)}$$

(iii) the diesters or polyesters blocked with an alcohol of formula (IV) below:

$$R_5O_2C - \text{[naphthalene]} - CO_2 - R_6O_2C - \text{[naphthalene]} - CO_2 - R_5 \quad \text{(IV)}$$

(iv) mixtures thereof;

in which:
- the radicals $R_5$, which may be identical or different, are each a linear or branched $C_1$-$C_{22}$ alkyl radical;
- the radicals $R_6$ and $R_7$, which may be identical or different, are each a linear or branched $C_1$-$C_6$ alkylene radical;
- k and l are numbers ranging from 1 to 100, preferably from 1 to 10 and more preferably from 2 to 7.

Among these naphthalenedicarboxylic acid diesters and polyesters of formula (II), (III) or (IV), 2,6-naphthalenedicarboxylic acid diesters and polyesters will preferably be used.

Among the polyesters corresponding to formula (IV) that will be selected are those resulting from the reaction of 2,6-naphthalenedicarboxylic acid and tripropylene glycol and blocked with 2-butyloctanol and also the polyesters corresponding to formula (IV) resulting from the reaction of 2,6-naphthalenedicarboxylic acid, tripropylene glycol and diethylene glycol and blocked with 2-ethylhexanol.

Among the naphthalene derivatives in accordance with the invention, diethylhexyl 2,6-naphthalate (INCI name) is used more particularly, for instance the product marketed under the trademark Hallbrite TQ by C. P. Hall.

Among the 4-hydroxybenzylidenemalonate derivatives or the 4-hydroxycinnamate derivatives that will preferentially be used are those of formula (V):

$$\text{(V)}$$

in which A is a chromophoric group that absorbs UV radiation, comprising two monovalent groups containing a carbonyl function;

$R_8$ is hydrogen, a linear or branched $C_1$-$C_8$ alkyl radical or a linear or branched $C_1$-$C_8$ alkoxy radical, $R_9$ is hydrogen or a linear or branched $C_1$-$C_8$ alkyl radical.

Among these compounds, the ones that will be used more preferentially are those of formula (Va) below:

$$\text{(Va)}$$

in which:
- $R_8$ is hydrogen, a linear or branched $C_1$-$C_8$ alkyl radical or a linear or branched $C_1$-$C_8$ alkoxy radical,
- $R_9$ is hydrogen or a linear or branched $C_1$-$C_8$ alkyl radical,
- $R_{10}$ is selected from —C(O)CH$_3$, —CO$_2$R$_{12}$, —C(O)NH$_2$, and —C(O)N(R$_{13}$)$_2$,
- X is O or NH,
- $R_{11}$ is a linear or branched $C_1$-$C_{30}$ alkyl radical,
- $R_{12}$ is a linear or branched $C_1$-$C_{20}$ alkyl radical,
- each $R_{13}$ independently is a linear or branched $C_1$-$C_8$ alkyl radical.

Among these compounds, the ones that will be used more preferentially are those of formula (Vb) or (Vc) below:

$$\text{(Vb)}$$

$$\text{(Vc)}$$

in which:
- $R_{10}$ is —CO$_2$R$_{12}$,
- $R_{11}$ is a linear or branched $C_1$-$C_8$ alkyl radical,
- $R_{12}$ is a linear or branched $C_1$-$C_8$ alkyl radical, and
- X is O.

The compound that will be used in particular is diethylhexyl syringylidenemalonate (INCI name) having the following formula:

such as the commercial product marketed under the trademark Oxynex ST by Merck.

Among the fluorene derivatives in accordance with the invention, use will preferably be made of those corresponding to one of the formulae (VI), (VII), (VIII), (IX), (X), (XI), (XII) and (XIII) below such as those described in U.S. Published Application Nos. 2004/00579912, 2004/00579914, 2004/00579916 and 2004/062726:

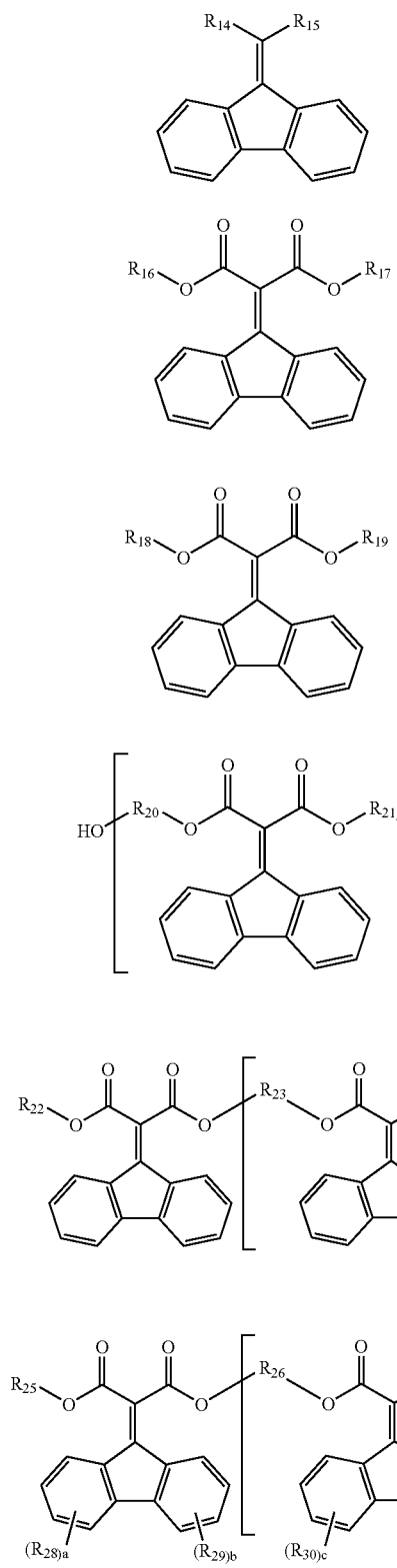

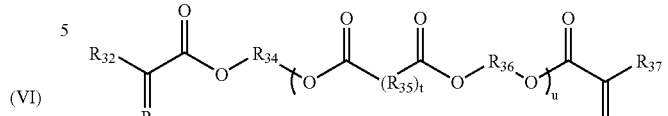

(XII)

(XIII)

in which:

the radicals $R_{14}$, $R_{15}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, and $R_{32}$, which may be identical or different, are each an optionally substituted linear or branched $C_1$-$C_{30}$ alkyl radical; an optionally substituted $C_3$-$C_8$ cycloalkyl radical; an optionally substituted monocyclic, bicyclic or tricyclic aryl radical; an optionally substituted monocyclic, bicyclic or tricyclic heteroaryl radical; an optionally substituted $C_3$-$C_{14}$ heterocycloalkyl radical; an amino or cyano group; an ester group of formula:

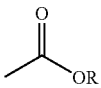

in which R is an optionally substituted linear or branched $C_1$-$C_{30}$ alkyl radical or an optionally substituted $C_3$-$C_8$ cycloalkyl radical;

the radicals $R_{33}$ and $R_{38}$, which may be identical or different, are each substituted or unsubstituted diphenylmethylene; substituted or unsubstituted 9H-fluorene;

the radical $R_{39}$ is an optionally substituted linear or branched $C_1$-$C_{30}$ alkyl radical; an optionally substituted linear or branched $C_1$-$C_{30}$ hydroxyalkyl radical; an optionally substituted $C_3$-$C_8$ cycloalkyl radical; an optionally substituted monocyclic, bicyclic or tricyclic aryl radical; an optionally substituted monocyclic, bicyclic or tricyclic heteroaryl radical; an optionally substituted $C_3$-$C_{14}$ heterocycloalkyl radical; an optionally substituted ether; an amino group;

the radicals $R_{40}$ and $R_4$, are each, independently of each other, hydrogen, an optionally substituted linear or branched $C_1$-$C_{30}$ alkyl radical; an optionally substituted linear or branched $C_1$-$C_{30}$ hydroxyalkyl radical; an optionally substituted $C_3$-$C_8$ cycloalkyl radical; an optionally substituted monocyclic, bicyclic or tricyclic aryl radical; an optionally substituted monocyclic, bicyclic or tricyclic heteroaryl radical; an optionally substituted $C_3$-$C_{14}$ heterocycloalkyl radical; an amino group, a cyano, hydroxyl, amide or imide, a halogen, an optionally substituted ether, an ester or a urethane;

q, r, s and t are numbers ranging from 1 to 100;

a, b, c, d, e and f are numbers ranging from 0 to 4, u is a number ranging from 0 to 100, and also mixtures of these compounds.

Among the compounds of formula (VI) that will be used more particularly are the compounds for which the radicals $R_{14}$ and $R_{15}$ are branched $C_1$-$C_{15}$ alkyl radicals and more particularly simultaneously are 2-ethylhexyl (i.e., the compound 2-ethylhexyl (9H-fluoren-9-ylidene)acetate).

Among the compounds of formula (VII) that will be used more particularly are the compounds for which the radicals $R_{16}$ and $R_{17}$ are branched $C_1$-$C_{15}$ alkyl radicals and more particularly are compounds for which the radicals $R_{16}$ and $R_{17}$ simultaneously are isopropyl or 2-ethylhexyl.

Mention may be made in particular of the compounds diisopropyl fluorenemalonate (or diisopropyl 9H-fluoren-9-ylidenemalonate) and bis(2-ethylhexyl) fluorenemalonate (or bis(2-ethylhexyl) 9H-fluoren-9-ylidenemalonate).

Among the compounds of formula (VIII) that will be used more particularly are the compounds for which the radicals $R_{18}$ and $R_{19}$ are branched $C_3$-$C_{20}$ alkyl radicals and more particularly simultaneously are 2-ethylhexyl.

Among the compounds of formula (X) that will be used more particularly are the compounds for which the radicals $R_{22}$, $R_{23}$ and $R_{24}$ are branched $C_1$-$C_{15}$ alkyl radicals and more particularly are compounds for which $R_{22}$ and $R_{24}$ are simultaneously 2-ethylhexyl.

Among the compounds of formula (XI) that will be used more particularly are the compounds for which the radicals $R_{25}$, $R_{26}$ and $R_{27}$ are branched $C_1$-$C_{15}$ alkyl radicals and more particularly are compounds for which $R_{25}$ and $R_{27}$ are simultaneously 2-ethylhexyl.

Among the compounds of formula (XII) that will be used more particularly are the compounds for which the radicals $R_{34}$ and $R_{36}$ are $C_1$-$C_{15}$ alkyl radicals, in particular 2-methylpropyl, $R_{35}$ is a linear $C_1$-$C_{15}$ alkyl and especially n-butyl; the radicals $R_{32}$ and $R_{37}$ simultaneously are cyano and the radicals $R_{33}$ and $R_{38}$ are diphenylmethylene.

Use will be made more particularly of the polymer having the following structure:

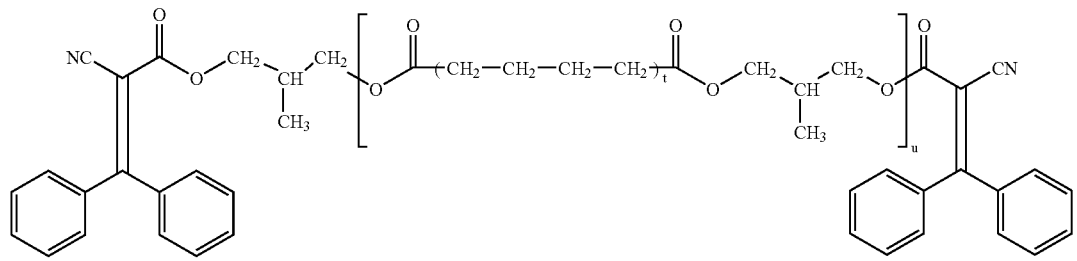

in which t=1 and u is a number ranging from 2 to 10.

Among the compounds of formula (XIII) that will preferably be used are the compounds for which e and f are equal to 0 and the radical $R_{39}$ is a branched $C_3$-$C_{20}$ alkyl radical or a $C_1$-$C_{15}$ hydroxyalkyl radical.

Use will be made in particular of the compounds of formula (XIII) for which the radical $R_{39}$ is a hydroxyalkyl selected from among hydroxyethyl, 1-hydroxypropyl, 2-hydroxypropyl, 1-hydroxy-n-butyl; 1-hydroxy-1-methylpropyl, 1-hydroxy-2,2-dimethylpropyl and 2-hydroxy-2-methylpropyl.

Use will be made more particularly of the compound of formula (XIII) for which e and f are equal to 0 and the radical $R_{39}$ is 2-ethylhexyl, i.e., the compound 2-ethylhexyl cyano(9H-fluoren-9-ylidene)acetate or octofluorene.

Among the piperidinol salts in accordance with the invention, the ones that may preferably be used are those of formula (XV) below:

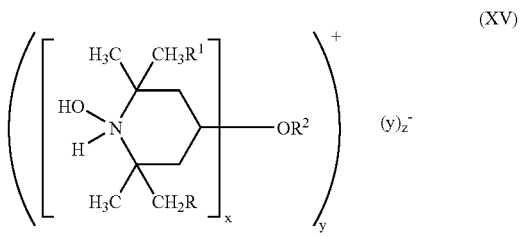

in which:
$R^1$ is hydrogen or methyl,
x is 1 or 2, 1) when x is equal to 1:
$R^2$ is hydrogen; a $C_1$-$C_{18}$ alkyl radical; a $C_2$-$C_{18}$ alkenyl radical; a propargyl radical; a glycidyl group; a $C_2$-$C_{50}$ alkyl radical interrupted with 1 to 20 oxygen atoms, the said alkyl being substituted with 1 to 10 hydroxyl groups or alternatively simultaneously interrupted with the said oxygen atoms and substituted with the said hydroxyl groups; a $C_1$-$C_4$ alkyl radical substituted with a carboxyl group or a group —COOZ in which Z is hydrogen, a $C_1$-$C_4$ alkyl radical, phenyl, a $C_1$-$C_4$ alkyl radical substituted with a group $(COO^-)_p$ $M^{p+}$ wherein p is an integer ranging from 1 to 3 and M is a metal ion from Groups 1, 2 and 3 of the Periodic Table or Zn, Cu, Ni or Co, or alternatively M is a group $N^{p+}(R'')_4$ wherein R" is a $C_1$-$C_8$ alkyl or a benzyl;

2) when x is 2:
R' is a $C_1$-$C_{12}$ alkylene radical; a $C_4$-$C_{12}$ alkenylene radical; a xylylene radical; a $C_1$-$C_{50}$ alkylene radical interrupted with 1 to 20 oxygen atoms, the said alkyl being substituted with 1 to 10 hydroxyl groups or alternatively simultaneously interrupted with the said oxygen atoms and substituted with the said hydroxyl groups;
Y is an organic or mineral anion;

the total charge of cations y being equal to the total charge of anions z.

Among the anions Y that may be mentioned are phosphate, phosphonate, carbonate, bicarbonate, nitrate, chloride, bromide, bisulfite, sulfite, bisulfate, borate, formate, acetate, benzoate, citrate, oxalate, tartrate, acrylate, poly-acrylate, fumarate, maleate, itaconate, glycolate, gluconate, malate, mandelate, tiglate, ascorbate, polymethacrylate, a carboxylate of n itrilotriacetic acid, hydroxyethylened iaminetriacetic acid, ethylenediaminetetraacetic acid, diethylenediaminepentaacetic acid, diethylenetriaminepentamethylene phosphonate, an alkylsulfonate or an arylsulfonate.

Use will be made in particular of the compounds of formula (XIV) for which $R^1$ and $R^2$ are each hydrogen, x=1 and Y is a citrate anion, and even more particularly the compound tris(tetramethylhydroxypiperidinol) citrate of structure:

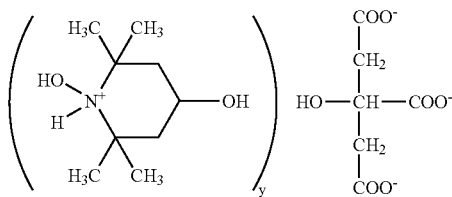

with y=3, such as the commercial product marketed under the name Tinoguard Q or Tinoguard S-FX by Ciba-Geigy.

The compounds capable of accepting the triplet state energy of the dibenzoylmethane derivatives in accordance with the invention may be present in the compositions in accordance with the invention in contents ranging from 0.1% to 25% by weight, more preferentially from 0.2% to 10% by weight and even more preferentially from 0.2% to 7% by weight relative to the total weight of the composition.

According to the present invention, the photostabilizing mixture of compound capable of accepting the triplet state energy of the dibenzoylmethane derivatives/amide oil will be used in a sufficient amount for obtaining an appreciable and significant improvement in the photostability of the dibenzoylmethane derivative in a given composition. This minimum amount of photostabilizer to be used may vary according to the amount of dibenzoylmethane present at the start in the composition and according to the nature of the cosmetically acceptable support adopted for the composition. It may be determined without any difficulty by means of a standard test for measuring photostability.

The compositions in accordance with the invention may also comprise other additional UV-A-active and/or UV-B-active organic or mineral photoprotective agents that are water-soluble or liposoluble or insoluble in the cosmetic solvents commonly used.

The additional organic photoprotective agents are selected especially from among anthranilates; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303,549, DE-197,26 184 and EP-893,119; benzoxazole derivatives such as those described in EP-0,832,642; EP-1,027,883, EP-1,300,137 and DE-101,62,844; screening polymers and screening silicones such as those described especially in WO 93/04665; dimers derived from α-alkylstyrene, such as those described in DE-198,55,649; 4,4-diarylbutadienes such as those described in EP-0,967,200, DE-197,46,654, DE-197,55,649, EP-A-1,008,586, EP-1,133,980 and EP-133,981, and mixtures thereof.

As examples of additional organic photoprotective agents, representative are those denoted hereinbelow under their INCI name:

Para-Aminobenzoic Acid Derivatives:
PABA,
Ethyl PABA,
Ethyl dihydroxypropyl PABA,
Ethylhexyl dimethyl PABA marketed in particular under the name "Escalol 507" by ISP,
Glyceryl PABA,
PEG-25 PABA marketed under the name "Uvinul P25" by BASF.

Salicylic Derivatives:
Homosalate marketed under the name "Eusolex HMS" by Rona/EM Industries,
Ethylhexyl salicylate marketed under the name "Neo Heliopan OS" by Haarmann and Reimer,
Dipropylene glycol salicylate marketed under the name "Dipsal" by Scher,
TEA salicylate marketed under the name "Neo Heliopan TS" by Haarmann and Reimer.

β,β-Diphenylacrylate Derivatives:
Octocrylene marketed in particular under the trademark "Uvinul N539" by BASF,
Etocrylene marketed in particular under the trademark "Uvinul N35" by BASF.

Benzophenone Derivatives:
Benzophenone-1 marketed under the trademark "Uvinul 400" by BASF,
Benzophenone-2 marketed under the trademark "Uvinul D50" by BASF,
Benzophenone-3 or Oxybenzone marketed under the trademark "Uvinul M40" by BASF,
Benzophenone-4 marketed under the trademark "Uvinul MS40" by BASF,
Benzophenone-5,
Benzophenone-6 marketed under the trademark "Helisorb 11" by Norquay,
Benzophenone-8 marketed under the trademark "Spectra-Sorb UV-24" by American Cyanamid,
Benzophenone-9 marketed under the trademark "Uvinul DS-49" by BASF,
Benzophenone-12
Diethylaminohydroxybenzoylhexyl benzoate marketed under the trademark "Uvinul A Plus" by BASF.

Benzylidenecamphor Derivatives:
3-Benzylidenecamphor manufactured under the name "Mexoryl SD" by Chimex,
4-Methylbenzylidenecamphor marketed under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.

Phenylbenzimidazole Derivatives:
Phenylbenzimidazolesulfonic acid marketed in particular under the trademark "Eusolex 232" by Merck,
Disodium phenyl dibenzimidazole tetrasulfonate marketed under the trademark "Neo Heliopan AP" by Haarmann and Reimer.

Phenylbenzotriazole Derivatives:
Drometrizole trisiloxane marketed under the name "Silatrizole" by Rhodia Chimie, Methylenebis(benzotriazolyl)tetramethylbutylphenol marketed in solid form under the trademark "MIXXIM BB/100" by Fairmount Chemical, or in micronized form as an aqueous dispersion under the trademark "Tinosorb M" by Ciba Specialty Chemicals.

Triazine Derivatives:

Bis(ethylhexyloxyphenol)methoxyphenyl triazine marketed under the trademark "Tinosorb S" by Ciba-Geigy, Ethylhexyltriazone marketed in particular under the trademark "Uvinul T150" by BASF, Diethylhexylbutamidotriazone marketed under the trademark "Uvasorb HEB" by Sigma 3V, 2,4,6-tris(diisobutyl 4'-aminobenzalmalonate)-s-triazine.

Anthranilic Derivatives:

Menthyl anthranilate marketed under the trademark "Neo Heliopan MA" by Haarmann and Reimer.

Imidazoline Derivatives:

Ethylhexyldimethoxybenzylidenedioxoimidazoline propionate.

Benzalmalonate Derivatives:

Polyorganosiloxane containing benzalmalonate functions, for instance Polysilicone-15, marketed under the trademark "Parsol SLX" by Hoffmann LaRoche.

4,4-Diarylbutadiene Derivatives:

1,1-Dicarboxy(2,2'-dimethylpropyl)-4,4-diphenylbutadiene.

Benzoxazole Derivatives:

2,4-bis[5-(1-dimethylpropyl)benzoxazol-2-yl(4-phenyl)imino]-6-(2-ethylhexyl)imino-1,3,5-triazine marketed under the name Uvasorb K2A by Sigma 3V and mixtures thereof.

The preferred additional organic photoprotective agents are selected from among:

Ethylhexyl salicylate,
Octocrylene,
Phenylbenzimidazolesulfonic acid,
Benzophenone-3,
Benzophenone-4,
Benzophenone-5,
Diethylaminohydroxybenzoylhexyl benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Ethylhexyl Triazone,
Bis(ethylhexyloxyphenol)methoxyphenyltriazine
Diethylhexyl Butamido Triazone,
Drometrizole trisiloxane,
Polysilicone-15,
1,1-Dicarboxy(2,2'-dimethylpropyl)-4,4-diphenylbutadiene,
2,4-Bis[5-1 (dimethylpropyl)benzoxazol-2-yl(4-phenyl)imino]-6-(2-ethylhexyl)imino-1,3,5-triazine, and mixtures thereof.

The additional mineral photoprotective agents are selected from among pigments and even more preferably nanopigments (mean size of the primary particles: generally from 5 nm to 100 nm and preferably from 10 nm to 50 nm) of treated or untreated metal oxides such as, for example, nanopigments of titanium oxide (amorphous or crystallized in rutile and/or anatase form), of iron oxide, of zinc oxide, of zirconium oxide or of cerium oxide.

The treated nanopigments are pigments that have undergone one or more surface treatments of chemical, electronic, mechanochemical and/or mechanical nature with compounds as described, for example, in *Cosmetics & Toiletries*, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen or elastin), alkanolamines, silicon oxides, metal oxides, sodium hexametaphosphate, alumina or glycerol.

The treated nanopigments may more particularly be titanium oxides treated with:

silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide, alumina and aluminum stearate, such as the product "Microtitanium Dioxide MT 100 T" from the company Tayca, alumina and aluminum laurate, such as the product "Microtitanium Dioxide MT 100 S" from the company Tayca, iron oxides and iron stearate, such as the product "Microtitanium Dioxide MT 100 F" from the company Tayca, silica, alumina and silicone, such as the products "Microtitanium Dioxide MT 100 SAS", "Microtitanium Dioxide MT 600 SAS" and "Microtitanium Dioxide MT 500 SAS" from the company Tayca, sodium hexametaphosphate, such as the product "Microtitanium Dioxide MT 150 W" from the company Tayca, octyltrimethoxysilane, such as the product "T-805" from the company Degussa, alumina and stearic acid, such as the product "UVT-M160" from the company Kemira, alumina and glycerol, such as the product "UVT-M212" from the company Kemira, alumina and silicone, such as the product "UVT-M262" from the company Kemira.

Other titanium oxide nanopigments treated with a silicone are preferably $TiO_2$ treated with octyltrimethylsilane and for which the mean size of the elementary particles is from 25 and 40 nm, such as the product marketed under the trademark "T805" by Degussa Silices, $TiO_2$ treated with a polydimethylsiloxane and for which the mean size of the elementary particles is 21 nm, such as the product marketed under the trademark "70250 Cardre UF TiO2SI3" by Cardre, anatase/rutile $TiO_2$ treated with a polydimethylhydrogenosiloxane and for which the mean size of the elementary particles is 25 nm, such as the product marketed under the trademark "Microtitanium Dioxide USP Grade Hydrophobic" by Color Techniques.

The uncoated titanium oxide nanopigments are marketed, for example, by Tayca under the trademarks "Microtitanium Dioxide MT 500 B" or "Microtitanium Dioxide MT 600 B", by Degussa under the name "P 25", by Wacker under the name "Oxyde de titane transparent PW", by Myoshi Kasei under the name "UFTR", by Tomen under the name "ITS" and by Tioxide under the name "Tioveil AQ".

The uncoated zinc oxide nanopigments are, for example:

those marketed under the name "Z-Cote" by Sunsmart;

those marketed under the name "Nanox" by Elementis;

those marketed under the name "Nanogard WCD 2025" by Nanophase Technologies.

The coated zinc oxide nanopigments are, for example:

those marketed under the name "Zinc Oxide CS-5" by Toshibi (ZnO coated with polymethylhydrogenosiloxane);

those marketed under the name "Nanogard Zinc Oxide FN" by Nanophase Technologies (as a 40% dispersion in Finsolv TN, $C_{12}$-$C_{15}$ alkyl benzoate);

those marketed under the name "Daitopersion ZN-30" and "Daitopersion ZN-50" by Daito (dispersions in cyclopolymethylsiloxane/oxyethylenated polydimethylsiloxane, containing 30% or 50% of nanozinc oxides coated with silica and polymethylhydrogenosiloxane);

those marketed under the name "NFD Ultrafine ZNO" by Daikin (ZnO coated with perfluoroalkyl phosphate and copolymer based on perfluoroalkylethyl as a dispersion in cyclopentasiloxane);

those marketed under the name "SPD-Z1" by Shin-Etsu (ZnO coated with silicone-grafted acrylic polymer, dispersed in cyclodimethylsiloxane);

those marketed under the name "Escalol Z100" by ISP (alumina-treated ZnO dispersed in an ethylhexyl methoxycinnamate/PVP-hexadecene/methicone copolymer mixture);

those marketed under the name "Fuji ZNO-SMS-10" by Fuji Pigment (ZnO coated with silica and polymethylsilsesquioxane);

those marketed under the name "Nanox Gel TN" by Elementis (ZnO dispersed at a concentration of 55% in $C_{12}$-$C_{15}$ alkyl benzoate with hydroxystearic acid polycondensate).

The uncoated cerium oxide nanopigments are marketed under the name "Colloidal Cerium Oxide" by Rhone-Poulenc.

The uncoated iron oxide nanopigments are marketed, for example, by Arnaud under the names "Nanogard WCD 2002 (FE 45B)", "Nanogard Iron FE 45 BL AQ", "Nanogard FE 45R AQ" and "Nanogard WCD 2006 (FE 45R)" or by Mitsubishi under the name "TY-220", The coated iron oxide nanopigments are marketed, for example, by Arnaud under the names "Nanogard WCD 2008 (FE 45B FN)", "Nanogard WCD 2009 (FE 45B 556)", "Nanogard FE 45 BL 345" and "Nanogard FE 45 BL" or by BASF under the name "Transparent Iron Oxide".

Also exemplary are the mixtures of metal oxides, especially of titanium dioxide and of cerium dioxide, including the silica-coated equal-weight mixture of titanium dioxide and of cerium dioxide, marketed by Ikeda under the name "Sunveil A", and also the alumina, silica and silicone-coated mixture of titanium dioxide and of zinc dioxide, such as the product "M 261" marketed by Kemira, or the alumina, silica and glycerol-coated mixture of titanium dioxide and of zinc dioxide, such as the product "M 211" marketed by Kemira.

The nanopigments may be introduced into the compositions according to the invention in unmodified form or in the form of pigmentary paste, i.e., as a mixture with a dispersant, as described, for example, in GB-A-2,206,339.

The additional photoprotective agents are generally present in the compositions according to the invention in proportions ranging from 0.01% to 20% by weight relative to the total weight of the composition and preferably ranging from 0.1% to 10% by weight relative to the total weight of the composition.

The compositions according to the invention may also contain agents for artificially tanning and/or browning the skin (self-tanning agents) and more particularly dihydroxyacetone (DHA). They are preferably present in amounts ranging from 0.1% to 10% by weight relative to the total weight of the composition.

The compositions in accordance with the present invention may also comprise standard cosmetic adjuvants selected especially from among fatty substances, organic solvents, ionic or nonionic, hydrophilic or lipophilic thickeners, softeners, humectants, opacifiers, stabilizers, emollients, silicones, anti-foams, fragrances, preservatives, anionic, cationic, nonionic, zwitterionic or amphoteric surfactants, active agents, fillers, polymers, propellants, acidifying or basifying agents or any other ingredient usually used in cosmetics and/or dermatology.

The fatty substances may be an oil or a wax or mixtures thereof. The term "oil" means a compound that is liquid at room temperature. The term "wax" means a compound that is solid or substantially solid at room temperature and whose melting point is generally greater than 35° C.

Oils that may be mentioned include mineral oils (paraffin); plant oils (sweet almond oil, macadamia oil, grapeseed oil or jojoba oil); synthetic oils, for instance perhydrosqualene, fatty alcohols, fatty acids or fatty esters (for instance the $C_{12}$-$C_{15}$ alkyl benzoate marketed under the trademark "Finsolv TN" of "Witconol TN" by Witco, octyl palmitate, isopropyl lanolate and triglycerides, including capric/caprylic acid triglycerides), oxyethylenated or oxypropylenated fatty esters and ethers; silicone oils (cyclomethicone and polydimethylsiloxanes, or PDMS) or fluoro oils, and polyalkylenes.

Waxy compounds that may be mentioned include paraffin, carnauba wax, beeswax and hydrogenated castor oil.

Among the organic solvents that may be mentioned are lower alcohols and polyols. These polyols may be selected from glycols and glycol ethers, for instance ethylene glycol, propylene glycol, butylene glycol, dipropylene glycol or diethylene glycol.

Hydrophilic thickeners that may be mentioned include carboxyvinyl polymers such as the Carbopol products (carbomers) and the Pemulen products (acrylate/C10-C30-alkylacrylate copolymer); polyacrylamides, for instance the crosslinked copolymers marketed under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) marketed by Hoechst under the trademark "Hostacerin AMPS" (CTFA name: ammonium polyacryldimethyltauramide); cellulose-based derivatives such as hydroxyethylcellulose; polysaccharides and especially gums such as xanthan gum; and mixtures thereof.

Lipophilic thickeners that may be mentioned include modified clays such as hectorite and its derivatives, for instance the products marketed under the name bentone.

Among the active agents that are representative are:
anti-pollution agents and/or free-radical scavengers;
depigmenting agents and/or propigmenting agents;
anti-glycation agents;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
desquamating agents;
moisturizers;
anti-inflammatory agents;
agents acting on the energy metabolism of cells;
insect repellants;
substance P or CGRP antagonists.

Needless to say, one skilled in this art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be formulated according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion, a powder or a solid tube, and may optionally be packaged as an aerosol and may be in the form of a mousse or a spray.

The compositions according to the invention are preferably in the form of an oil-in-water or water-in-oil emulsion.

The emulsions generally contain at least one emulsifier selected from among amphoteric, anionic, cationic and nonionic emulsifiers, which are used alone or as a mixture. The emulsifiers are appropriately selected according to the emulsion to be obtained (W/O or O/W).

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, marketed under the name "DC 5225 C" by Dow Corning, and alkyldimethicone copolyols such as laurylmethicone copolyol marketed under the name "Dow Corning 5200 Formulation Aid" by Dow Corning; cetyldimethicone copolyol, such as the product marketed under the name Abil EM 90R by Goldschmidt, and the mixture of cetyldimethicone copolyol, of polyglyceryl isostearate (4 mol) and of hexyl laurate, marketed under the name Abil WE 09 by Goldschmidt. One or more co-emulsifiers may also be added thereto, which may be selected advantageously from among the group comprising polyol alkyl esters. Polyol alkyl esters that may especially be mentioned include glycerol and/or sorbitan esters, for example polyglyceryl isostearate, such as the product marketed under the name Isolan GI 34 by Goldschmidt, sorbitan isostearate, such as the product marketed under the name Arlacel 987 by ICI, sorbitan glyceryl isostearate, such as the product marketed under the name Arlacel 986 by ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside marketed, for example, by Henkel under the respective names Plantaren 2000 and Plantaren 1200, cetostearyl glucoside optionally as a mixture with cetostearyl alcohol, marketed, for example, under the name Montanov 68 by SEPPIC, under the name Tegocare CG90 by Goldschmidt and under the name Emulgade KE3302 by Henkel, and also arachidyl glucoside, for example in the form of a mixture of arachidyl alcohol, behenyl alcohol and arachidyl glucoside, marketed under the name Montanov 202 by SEPPIC. According to one particular embodiment of the invention, the mixture of the alkylpolyglucoside as defined above with the corresponding fatty alcohol may be in the form of a self-emulsifying composition as described, for example, in document WO-A-92/06778.

When it is an emulsion, the aqueous phase of this emulsion may comprise a nonionic vesicular dispersion prepared according to known processes (Bangham, Standish and Watkins, *J. Mol. Biol.*, 13, 238 (1965), FR-2,315,991 and FR-2,416,008).

The compositions according to the invention find application in a large number of treatments, especially cosmetic treatments, of the skin, the lips and the hair, including the scalp, especially for protecting and/or caring for the skin, the lips and/or the hair, and/or for making up the skin and/or the lips.

The present invention also features the use of the subject compositions as defined above for the manufacture of cosmetic products for treating the skin, the lips, the nails, the hair, the eyelashes, the eyebrows and/or the scalp, especially care products and makeup products.

The cosmetic compositions according to the invention may be administered (regime or regimen) for example, as care products and/or anti-sun products for the face and/or the body, of liquid to semi-liquid consistency, such as milks, more or less rich creams, cream-gels and pastes. They may optionally be packaged as an aerosol and may be in the form of mousses or sprays.

The compositions according to the invention in the form of vaporizable fluid lotions are applied to the skin or the hair in the form of fine particles by means of pressurization devices. The devices in accordance with the invention are well known to those skilled in the art and include non-aerosol pumps or "atomizers", aerosol containers comprising a propellant and also aerosol pumps using compressed air as propellant. The latter pumps are described in U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

COMPOSITION EXAMPLES 1 TO 3

The following compositions were prepared, the amounts being expressed as weight percentages.

| Phase | Composition | Formula 1 | Formula 2 | Formula 3 |
|---|---|---|---|---|
| Phase A | Polydimethylsiloxane | 0.5 | 0.5 | 0.5 |
| | Preservatives | 1 | 1 | 1 |
| | Stearic acid | 1.5 | 1.5 | 1.5 |
| | Glyceryl monostearate/PEG stearate mixture (100 EO) | 1 | 1 | 1 |
| | Mixture of cetylstearyl glucoside, cetyl alcohol and stearyl alcohol | 2 | 2 | 2 |

-continued

| Phase | Composition | Formula 1 | Formula 2 | Formula 3 |
|---|---|---|---|---|
| | Cetyl alcohol | 0.5 | 0.5 | 0.5 |
| | 4 tert-Butyl-4'-methoxydibenzoylmethane | 2 | 2 | 2 |
| | $C_{12}$-$C_{13}$ alkyl benzoate | 10 | 5 | 5 |
| | N-Lauroyl isopropyl sarcosinate (Eldew SL-205 - Ajimoto) | 10 | 20 | 20 |
| | 2,6-Diethylhexyl naphthalate (Hallbrite TQ from CP Hall) | 0.5 | — | — |
| | Diethylhexyl syringylidenemalonate (Oxynex ST from Merck) | — | 1 | — |
| | Tris(tetramethyl-hydroxypiperidinol) citrate (Tinoguard Q from Ciba-Geigy) | — | — | 2 (AM)* |
| Phase B | Deionized water | qs 100 | qs 100 | qs 100 |
| | Complexing agent | 0.1 | 0.1 | 0.1 |
| | Glycerol | 5 | 5 | 5 |
| | Xanthan gum | 0.2 | 0.2 | 0.2 |
| | Monocetyl phosphate | 1 | 1 | 1 |
| Phase C | Isohexadecane | 1 | 1 | 1 |
| | Acrylic acid/stearyl methacrylate copolymer | 0.2 | 0.2 | 0.2 |
| | Triethanolamine | qs pH | qs pH | qs pH |

*AM = active material

Method:

The aqueous phase (Phase B) containing all of its ingredients is heated to 80° C. on a water bath. The fatty phase (Phase A) containing all of its ingredients is heated to 80° C. on a water bath. A is emulsified in B with stirring of rotor-stator type (machine from the company Moritz). Phase C is incorporated and the mixture is allowed to cool to room temperature with moderate stirring. The triethanolamine is introduced so as to adjust the pH to the desired value at the end of manufacture.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, photostabilized, photoprotective cosmetic/dermatological composition, comprising (i) an effective UV-screening amount of at least one dibenzoylmethane sunscreen and an effective photostabilizing amount of (ii) at least one oil containing at least one amide structural unit and (iii) at least one compound accepting the excited triplet level energy of said at least one dibenzoylmethane sunscreen, formulated into (iv) a topically applicable, cosmetically/dermatologically acceptable support therefor.

2. The photostable photoprotective cosmetic/dermatological composition as defined by claim 1, said at least one oil containing at least one amide structural unit being liquid and water-insoluble or water-immiscible at 25° C. and having no emulsifying properties.

3. The photostable photoprotective cosmetic/dermatological composition as defined by claim 1, said at least one oil containing at least one amide structural unit having the formula (I) below:

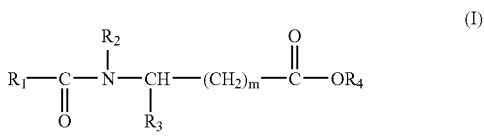

in which:
the radical $R_1$ is a saturated or unsaturated, aliphatic, cycloaliphatic or cyclic, optionally functionalized monovalent hydrocarbon-based radical having from 2 to 30 carbon atoms;
the radicals $R_2$, $R_3$ and $R_4$, which may be identical or different, are each hydrogen or saturated or unsaturated, aliphatic, cycloaliphatic or cyclic, optionally functionalized monovalent hydrocarbon-based radicals having from 1 to 30 carbon atoms;
m is 1 or 2.

4. The photostable photoprotective cosmetic/dermatological composition as defined by claim 3, said at least one dibenzoylmethane sunscreen being selected from the group consisting of:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl 4'-methoxydibenzoylmethane,
2,4-dimethyl-4'-methoxydibenzoylmethane,
2,6-dimethyl-4-tert-butyl-4'-methoxydibenzoylmethane,
and mixtures thereof.

5. The photostable photoprotective cosmetic/dermatological composition as defined by claim 3, said at least one dibenzoylmethane sunscreen comprising 4-(tert-butyl)-4'-methoxydibenzoylmethane (Butyl Methoxy Dibenzoylmethane).

6. The photostable photoprotective cosmetic/dermatological composition as defined by claim 3, said at least one dibenzoylmethane sunscreen ranging from 0.01% to 10% by weight relative to the total weight of the composition.

7. The photostable photoprotective cosmetic/dermatological composition as defined by claim 3, in which the at least one oil of formula (I) is selected from those wherein:
$R_1$ is a linear or branched $C_1$-$C_{22}$ alkyl radical; a linear or branched $C_2$-$C_{22}$ alkenyl radical; or an aryl radical;
$R_2$ is a hydrogen atom or a linear or branched $C_1$-$C_6$ alkyl radical;
$R_3$ is a hydrogen atom or a linear or branched $C_1$-$C_6$ alkyl radical; and
$R_4$ is a linear or branched $C_1$-$C_{10}$ alkyl radical or a linear or branched $C_2$-$C_{10}$ alkenyl radical or a sterol residue.

8. The photostable photoprotective cosmetic/dermatological composition as defined by claim 7, in which the at least one oil of formula (I) is selected from those wherein the group $R_1$(CO)— is an acyl group of an acid selected from the group consisting of toluic acid, capric acid, lauric acid, myristic acid, palmitic acid, stearic acid, behenic acid, linoleic acid, linolenic acid, oleic acid, isostearic acid, 2-ethylhexanoic acid, coconut oil fatty acids and palm kernel oil fatty acids; these acids optionally containing a hydroxyl group.

9. The photostable photoprotective cosmetic/dermatological composition as defined by claim 7, in which the at least one oil of formula (I) is selected from those in which the moiety —N(R$_2$)CH(R$_3$)(CH2)$_m$(CO)— of the amino acid ester is selected from those corresponding to the following amino acids:

glycine, alanine, valine, leucine, isoleucine, serine, threonine, proline, hydroxyproline, β-alanine, N-butyl-β-alanine, aminobutyric acid, aminocaproic acid, sarcosine and N-methyl-β-alanine.

10. The photostable photoprotective cosmetic/dermatological composition as defined by claim 7, in which the at least one oil of formula (I) is selected from those in which the moiety of the amino acid esters corresponding to the group OR$_4$ is obtained from alcohols selected from the group consisting of: methanol, ethanol, propanol, isopropanol, butanol, tert-butanol, isobutanol, 3-methyl-1-butanol, 2-methyl-1-butanol, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol and isostearyl alcohol.

11. The photostable photoprotective cosmetic/dermatological composition as defined by claim 7, in which the at least one oil of formula (I) comprises isopropyl N-lauroyl-sarcosinate of formula:

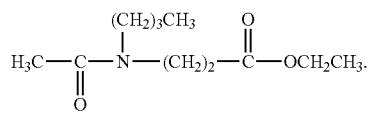

12. The photostable photoprotective cosmietic/dermatological composition as defined by claim 3, said at least one oil of formula (I) ranging from 0.1% to 40% by weight relative to the total weight of the composition.

13. The photostable photoprotective cosmetic/dermatological composition as defined by claim 3, said at least one compound accepting the excited triplet level energy of said at least one dibenzoylmethane sunscreen having an excited triplet level energy ranging from 40 kcal/mol to 70 kcal/mol.

14. The photostable photoprotective cosmetic/dermatological composition as defined by claim 3, said at least one compound accepting the excited triplet level energy of said at least one dibenzoylmethane sunscreen being selected from the group consisting of:
(i) naphthalene compounds;
(ii) 4-hydroxybenzylidenemalonate compounds or 4-hydroxycinnamate compounds;
(iii) fluorene compounds;
(iv) piperidinol salts;
(v) mixtures thereof.

15. The photostable photoprotective cosmetic/dermatological composition as defined by claim 14, said at feast one compound accepting the excited triplet level energy of said at least one dibenzoylmethane sunscreen comprising a naphthalene compound selected from the group consisting of:

(i) the diesters of formula (II) below:

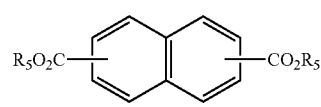

(ii) the diesters or polyesters of formula (III) below:

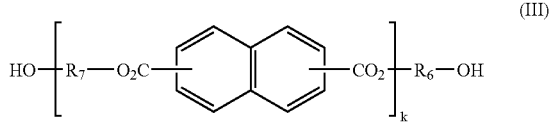

(iii) the diesters or polyesters blocked with an alcohol of formula (IV) below:

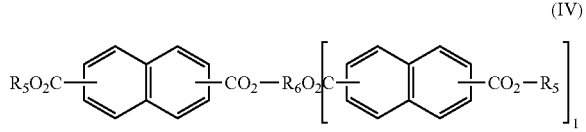

(iv) mixtures thereof;
in which:
the radicals R$_5$, which may be identical or different, are each a linear or branched C$_1$-C$_{22}$ alkyl radical;
the radicals R$_6$ and R$_7$, which may be identical or different, are each a linear or branched C$_1$-C$_6$ alkylene radical;
k and l are numbers ranging from 1 to 100.

16. The photostable photoprotective cosmetic/dermatological composition as defined by claim 15, comprising 2,6-naphthalene dicarboxylic acid diesters or polyesters.

17. The photostable photoprotective cosmetic/dermatological composition as defined by claim 16, comprising 2,6-diethylhexyl naphthalate.

18. The photostable photoprotective cosmetic/dermatological composition as defined by claim 15, comprising polyesters of 2,6-naphthalene dicarboxylic acid and tripropylene glycol blocked with 2-butyloctanol, or polyesters of 2,6-naphthalene dicarboxylic acid, tripropylene glycol and diethylene glycol blocked with 2-ethylhexanol.

19. The photostable photoprotective cosmetic/dermatological composition as defined by claim 14, said at least one compound accepting the excited triplet level energy of said at least one dibenzoylmethane sunscreen comprising a 4-hydroxybenzylidenemalonate compound or 4-hydroxycinnamate compound of formula (V):

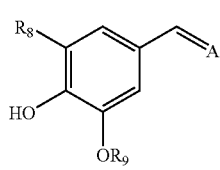

in which A is a chromophoric group that absorbs UV radiation, comprising two monovalent groups containing a carbonyl function;
R$_8$ is hydrogen, a linear or branched C$_1$-C$_8$ alkyl radical or a linear or branched C$_1$-C$_8$ alkoxy radical; and
R$_9$ is a linear or branched C$_1$-C$_8$ alkyl radical.

20. The photostable photoprotective cosmetic/dermatological composition as defined by claim 19, comprising at least one compound of formula (Va) below:

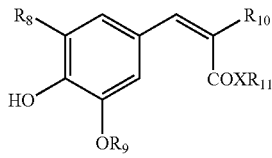
(Va)

in which:
R$_8$ is hydrogen, a linear or branched C$_1$-C$_8$ alkyl radical or a linear or branched C$_1$-C$_8$ alkoxy radical;
R$_9$ is hydrogen or a linear or branched C$_1$-C$_8$ alkyl radical;
R$_{10}$ is selected from —C(O)CH$_3$, —CO$_2$R$_{12}$, —C(O)NH$_2$, and —C(O)N(R$_{13}$)$_2$;
X is O or NH;
R$_{11}$ is a linear or branched C$_1$-C$_{30}$ alkyl radical; and
R$_{12}$ is a linear or branched C$_1$-C$_{20}$ alkyl radical; each R$_{13}$ independently is a linear or branched C$_1$-C$_8$ alkyl radical.

21. The photostable photoprotective cosmetic/dermatological composition as defined by claim 19, comprising at least one compound of formula (Vb) or (Vc) below:

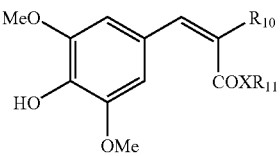
(Vb)

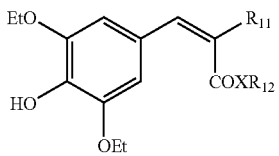
(Vc)

in which
R$_{10}$ is —CO$_2$R$_{12}$;
R$_{11}$ is a linear or branched C$_1$-C$_8$ alkyl radical;
R$_{12}$ is a linear or branched C$_1$-C$_8$ alkyl radical; and
X is O.

22. The photostable photoprotective cosmetic/dermatological composition as defined by claim 21, comprising diethylhexyl syringylidenemalonate having the following formula:

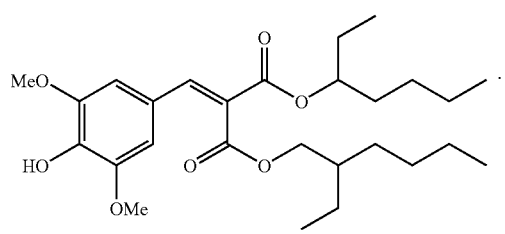

23. The photostable photoprotective cosmetic/dermatological composition as defined by claim 14, said at least one compound accepting the excited triplet level energy of said at least one dibenzoylmethane sunscreen comprising at least one fluorene compound having one of the formulae (VI) (VII), (VIII), (IX), (X), (XI), (XII) and (XIII) below:

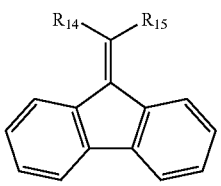
(VI)

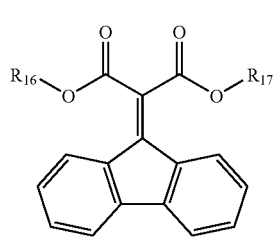
(VII)

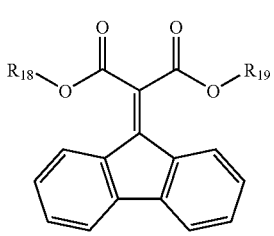
(VIII)

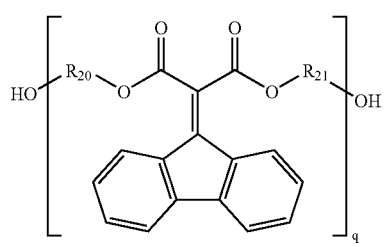
(IX)

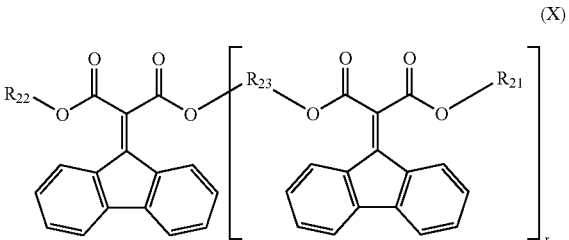
(X)

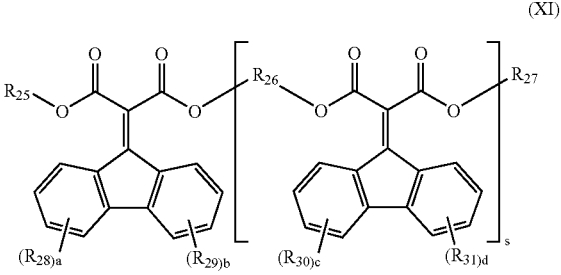
(XI)

-continued

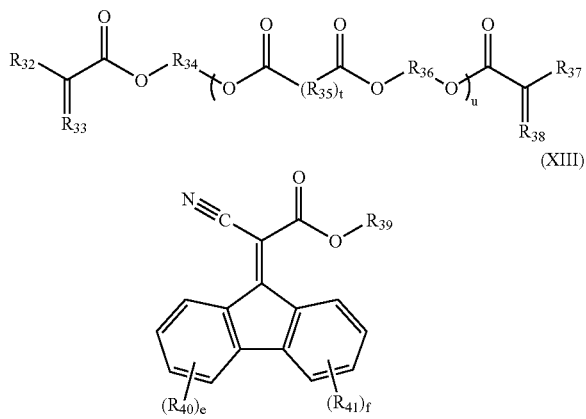

in which:

the radicals $R_{14}$, $R_{15}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, and $R_{32}$, which may be identical or different, are an optionally substituted linear or branched $C_1$-$C_{30}$ alkyl radical; an optionally substituted $C_3$-$C_8$ cycloalkyl radical; an optionally substituted monocyclic, bicyclic or tricyclic aryl radical; an optionally substituted monocyclic, bicyclic or tricyclic heteroaryl radical; an optionally substituted $C_3$-$C_{14}$ heterocycloalkyl radical; an amino or cyano group; an ester group of formula:

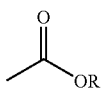

in which R is an optionally substituted linear or branched $C_1$-$C_{30}$ alkyl radical or an optionally substituted $C_3$-$C_8$ cycloalkyl radical;

the radicals $R_{33}$ and $R_{38}$, which may be identical or different, are each substituted or unsubstituted diphenylmethylene; substituted or unsubstituted 9H-fluorene;

the radical $R_{39}$ is an optionally substituted linear or branched $C_1$-$C_{30}$ alkyl radical; an optionally substituted linear or branched $C_1$-$C_{30}$ hydroxyalkyl radical; an optionally substituted $C_3$-$C_8$ cycloalkyl radical; an optionally substituted monocyclic, bicyclic or tricyclic aryl radical; an optionally substituted monocyclic, bicyclic or tricyclic heteroaryl radical; an optionally substituted $C_3$-$C_{14}$ heterocycloalkyl radical; an optionally substituted ether, an amino group;

the radicals $R_{40}$ and $R_{41}$ are each, independently of each other, hydrogen, an optionally substituted linear or branched $C_1$-$C_{30}$ alkyl radical; an optionally substituted linear or branched $C_1$-$C_{30}$ hydroxyalkyl radical; an optionally substituted $C_3$-$C_8$ cycloalkyl radical; an optionally substituted monocyclic, bicyclic or tricyclic aryl radical; an optionally substituted monocyclic, bicyclic or tricyclic heteroaryl radical; an optionally substituted $C_3$-$C_{14}$ heterocycloalkyl radical; an amino group, a cyano, hydroxyl, amide or imide, a halogen, an optionally substituted ether, an ester or a urethane;

q, r, s and t are numbers ranging from 1 to 100;

a, b, c, d, e and f are numbers ranging from 0 to 4, u is a number ranging from 0 to 100, and also mixtures of these compounds.

24. The photostable photoprotective cosmetic/dermatological composition as defined by claim 23, comprising at least one compound of formula (VI) wherein the radicals $R_{14}$ and $R_{15}$ are each branched $C_1$-$C_{15}$ alkyl radicals.

25. The photostable photoprotective cosmetic/dermatological composition as defined by claim 24, comprising the compound 2-ethylhexyl (9H-fluoren-9-ylidene)acetate.

26. The photostable photoprotective cosmetic/dermatological composition as defined by claim 23, comprising at least one compound of formula (VII) wherein the radicals $R_{16}$ and $R_{17}$ are each branched $C_1$-$C_{15}$ alkyl radicals.

27. The photostable photoprotective cosmetic/dermatological composition as defined by claim 26, comprising the compounds diisopropyl fluorenemalonate and/or bis(2-ethylhexyl) fluorenemalonate.

28. The photostable photoprotective cosmetic/dermatological composition as defined by claim 23, comprising at least one compound of formula (VIII) wherein the radicals $R_{18}$ and $R_{19}$ are each branched $C_3$-$C_{20}$ alkyl radicals.

29. The photostable photoprotective cosmetic/dermatological composition as defined by claim 23, comprising at least one compound of formula (X) wherein the radicals $R_{22}$, $R_{23}$ and $R_{24}$ are each branched $C_1$-$C_{15}$ alkyl radicals.

30. The photostable photoprotective cosmetic/dermatological composition as defined by claim 23, comprising at least one compound of formula (XI) wherein the radicals $R_{25}$, $R_{26}$ and $R_{27}$ are each branched $C_1$-$C_{15}$ alkyl radicals.

31. The photostable photoprotective cosmetic/dermatological composition as defined by claim 23, comprising at least one compound of formula (XII) wherein the radicals $R_{34}$ and $R_{36}$ are each $C_1$-$C_{15}$ alkyl radicals, $R_{35}$ is a linear $C_1$-$C_{15}$ alkyl radical; the radicals $R_{32}$ and $R_{37}$ simultaneously are each cyano and the radicals $R_{33}$ and $R_{38}$ are each diphenylmethylene.

32. The photostable photoprotective cosmetic/dermatological composition as defined by claim 31, said at least one fluorene compound of formula (XII) comprising the polymer having the following structure:

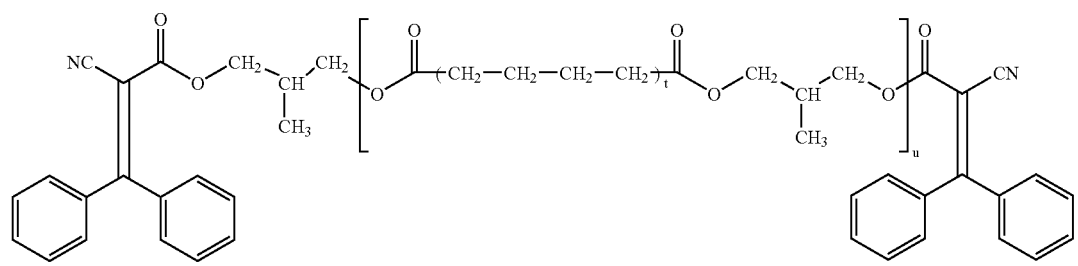

in which t=1 and u is a number ranging from 2 to 10.

33. The photostable photoprotective cosmetic/dermatological composition as defined by claim 23, comprising at least one compound of formula (XIII) wherein e and f are equal to 0; and the radical $R_{39}$ is a branched $C_3$-$C_{20}$ alkyl radical or a $C_1$-$C_{15}$ hydroxyalkyl radical.

34. The photostable photoprotective cosmetic/dermatological composition as defined by claim 33, wherein formula (XIII) the radical $R_{39}$ is hydroxyethyl, 1-hydroxypropyl, 2-hydroxypropyl, 1-hydroxy-n-butyl, 1-hydroxy-1-methylpropyl, 1-hydroxy-2,2-dimethylpropyl or 2-hydroxy-2-methylpropyl.

35. The pholostable photoprotective cosmetic/dermatological composition as defined by claim 33, comprising the compound 2-ethylhexyl cyano(9H-fluoren-9-ylidene)acetate (or octolfuorene).

36. The photostable photoprotective cosmetic/dermatological composition as defined by claim 14, said at least one compound accepting the excited triplet level energy of said at least one dibenzoylmethane sunscreen comprising at least one piperidinol salt having the formula (XIV) below:

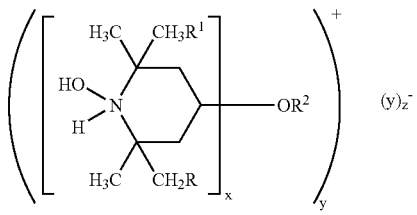

in which:
$R^1$ is hydrogen or methyl;
x is 1 or 2;
1) when x is equal to 1:
$R^2$ is hydrogen; a $C_1$-$C_{18}$ alkyl radical; a $C_2$-$C_{18}$ alkenyl radical; a propargyl radical; a glycidyl group; a $C_2$-$C_{50}$ alkyl radical interrupted with 1 to 20 oxygen atoms, the said alkyl being substituted with 1 to 10 hydroxyl groups or alternatively simultaneously interrupted with the said oxygen atoms and substituted with the said hydroxyl groups; a $C_1$-$C_4$ alkyl radical substituted with a carboxyl group or a group —COOZ in which Z is hydrogen, a $C_1$-$C_4$ alkyl radical, phenyl, a $C_1$-$C_4$ alkyl radical substituted with a group $(COO^{31})_p M^{p+}$ wherein p is an integer ranging from 1 to 3 and M is a metal ion from Groups 1, 2 and 3 of the Periodic Table or Zn, Cu, Ni or Co, or alternatively M is a group $N^{p+}(R")_4$ wherein R" is a $C_1$-$C_8$ alkyl radical or benzyl;
2) when x is 2:
R' is a $C_1$-$C_{12}$ alkylene radical; a $C_4$-$C_{12}$ alkenylene radical; a xylylene radical; a $C_1$-$C_{50}$ alkylene radical interrupted with 1 to 20 oxygen atoms, the said alkyl radical being substituted with 1 to 10 hydroxyl groups or alternatively simultaneously interrupted with the said oxygen atoms and substituted with the said hydroxyl groups;
Y is an organic or mineral anion; and
the total charge of cations y being equal to the total charge of anions z.

37. The photostable photoprotective cosmetic/dermatological composition as defined by claim 36, comprising at least one compound of formula (XIV) wherein $R^1$ and $R^2$ are each hydrogen; x=1 and Y is a citrate anion.

38. The photostable photoprotective cosmetic/dermatological composition as defined by claim 37, comprising tris(tetramethylhydroxypiperidinol) citrate of structure:

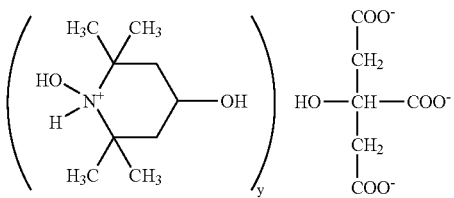

wherein y=3.

39. The photostable photoprotective cosmetic/dermatological composition as defined by claim 3, said at least one compound accepting the energy of the triplet state of the dibenzoylmethane sunscreen(s) ranging from 0.1% to 25% by weight relative to the total weight of the composition.

40. The photostable photoprotective cosmetic/dermatological composition as defined by claim 3, further comprising other UV-A-active and/or UV-B-active organic or mineral photoprotective agents that are water-soluble or liposoluble or insoluble in conventional cosmetic solvents.

41. The photostable photoprotective cosmetic/dermatological composition as defined by claim 40, comprising additional organic photoprotective agents selected from among anthranilates; salicylic derivatives, camphor derivatives; benzophenone derivatives; β,β-diphenylacrylate derivatives; benzotriazole derivatives; benzalmalonate derivatives; benzimidazole derivatives; imidazolines; bisbenzazolyl derivatives; p-aminobenzoic acid (PABA) derivatives; methylenebis(hydroxyphenylbenzotriazole) derivatives; benzoxazole derivatives; screening polymers and screening silicones; α-alkylstyrene-based dimers derivatives; 4,4-diarylbutadienes, and mixtures thereof.

42. The photostable photoprotective cosmetic/dermatological composition as defined by claim 41, said additional organic UV-screening agent(s) being selected from among the following compounds:
Ethylhexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Ethylhexyl Triazone,
Diethylhexyl Butamido Triazone,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine,
and mixtures thereof.

43. The photostable photoprotective cosmetic/dermatological composition as defined by claim 40, comprising additional mineral photoprotective agents selected from among treated or untreated metal oxide pigments or nanopigments.

44. The photostable photoprotective cosmetic/dermatological composition as defined by claim 43, said additional pigments or nanopigments being selected from among titanium oxide, zinc oxide, iron oxide, zirconium oxide and cerium oxide, and mixtures thereof.

45. The photostable photoprotective cosmetic/dermatological composition as defined by claim 3, further comprising at least one agent for artificially tanning and/or browning the skin.

46. The photostable photoprotective cosmetic/dermatological composition as defined by claim 3, further comprising at least one adjuvant selected from among fatty substances, organic solvents, ionic or nonionic, hydrophilic or lipophilic thickeners, softeners, humectants, opacifiers, stabilizers, emollients, silicones, anti-foams, fragrances, preservatives, anionic, cationic, nonionic, zwitterionic or amphoteric surfactants, active agents, fillers, polymers, propellants and acidifying or basifying agents.

47. The photostable photoprotective cosmetic/dermatological composition as defined by claim 3, formulated for the cosmetic treatment of the skin, the lips, the nails, the hair, the eyelashes, the eyebrows and/or the scalp.

48. The photostable photoprotective cosmetic/dermatological composition as defined by claim 3, formulated as a care product for the skin, the lips, the nails, the hair and/or the scalp.

49. The photostable photoprotective cosmetic/dermatological composition as defined by claim 3, formulated as a makeup product.

50. A process for photostabilizing a dibenzoylmethane sunscreen against UV-radiation, comprising combining same with at least one oil containing at least one amide structural unit and at least one compound accepting the excited triplet level energy of said dibenzoylmethane sunscreen.

51. A regime or regimen for photoprotecting the skin, the lips, the nails, the hair, the eyelashes, the eyebrows, and/or the scalp against the damaging effects of UV-radiation, comprising topically applying thereon a photostabilized photoprotective cosmetic/dermatological composition containing (i) an effective UV-screening amount of at least one dibenzoylmethane sunscreen and an effective photostabilizing amount of (ii) at least one oil containing at least one amide structural unit and (iii) at least one compound accepting the excited triplet level energy of said at least one dibenzoylmethane sunscreen, formulated into (iv) a topically applicable, cosmetically/dermatologically acceptable support therefor.

52. The photostable photoprotective cosmetic/dermatological composition as defined by claim 3, formulated as a water-in-oil or oil-in-water emulsion.

* * * * *